(12) United States Patent
Haynes et al.

(10) Patent No.: US 7,502,443 B1
(45) Date of Patent: Mar. 10, 2009

(54) RADIATION THERAPY MACHINE WITH TRIPLE KV/MV IMAGING

(75) Inventors: Stephen E. Haynes, Alameda, CA (US); Michiel T. vanderPols, Nieuwegein (NL)

(73) Assignees: Acceletronics Digital Imaging LLC, Exton, PA (US); Cablon Medical B.V., Nieuwegein (NL)

( * ) Notice: Subject to any disclaimer, the term of this patent is extended or adjusted under 35 U.S.C. 154(b) by 0 days.

(21) Appl. No.: 11/936,126

(22) Filed: Nov. 7, 2007

(51) Int. Cl.
*A61B 6/02* (2006.01)
(52) U.S. Cl. .......................... 378/65; 378/68; 378/205
(58) Field of Classification Search ................... 378/65, 378/68, 205
See application file for complete search history.

(56) References Cited

U.S. PATENT DOCUMENTS

| | | | |
|---|---|---|---|
| 4,995,068 A | | 2/1991 | Chou et al. ................. 378/189 |
| 5,207,223 A | * | 5/1993 | Adler .......................... 600/427 |
| 5,446,548 A | | 8/1995 | Gerig et al. ................. 356/375 |
| 5,724,400 A | * | 3/1998 | Swerdloff et al. ............. 378/65 |
| 6,094,152 A | * | 7/2000 | Cheng ......................... 341/132 |
| 6,307,914 B1 | * | 10/2001 | Kunieda et al. ............... 378/65 |
| 6,516,046 B1 | * | 2/2003 | Frohlich et al. ............... 378/65 |
| 6,842,502 B2 | * | 1/2005 | Jaffray et al. ................. 378/65 |
| 6,914,959 B2 | * | 7/2005 | Bailey et al. ................. 378/65 |
| 7,188,999 B2 | * | 3/2007 | Mihara et al. .............. 378/197 |
| 7,207,715 B2 | * | 4/2007 | Yue ............................. 378/205 |
| 7,227,925 B1 | | 6/2007 | Mansfield et al. ............. 378/65 |
| 7,239,684 B2 | | 7/2007 | Hara et al. .................... 378/65 |
| 7,418,079 B2 | * | 8/2008 | Schildkraut et al. .......... 378/65 |
| 2004/0184579 A1 | | 9/2004 | Mihara et al. ................. 378/65 |
| 2006/0067468 A1 | | 3/2006 | Rietzel ......................... 378/65 |

* cited by examiner

*Primary Examiner*—Edward J Glick
*Assistant Examiner*—Thomas R Artman
(74) *Attorney, Agent, or Firm*—Bernhard P. Molldrem, Jr.

(57) ABSTRACT

A triple imager arrangement is mounted onto a linear accelerator, providing pre- or post-treatment images of a patient, for verification and monitoring of patient position. Left and right diagnostic radiation sources mounted onto the treatment head. The triple imager arrangement is mounted on the gantry counterweight, with a portal imager and left and right diagnostic image detectors. Image-forming plates of the portal imager and the diagnostic imagers are positioned perpendicular to the therapy beam central axis, and perpendicular to the central axes of the diagnostic sources. The image forming plates are the same given distance X from the respective source. The resulting image information can be used in conjunction with an assistance module for assisting the linear accelerator therapist in accurate adjustment of the patient position.

6 Claims, 2 Drawing Sheets

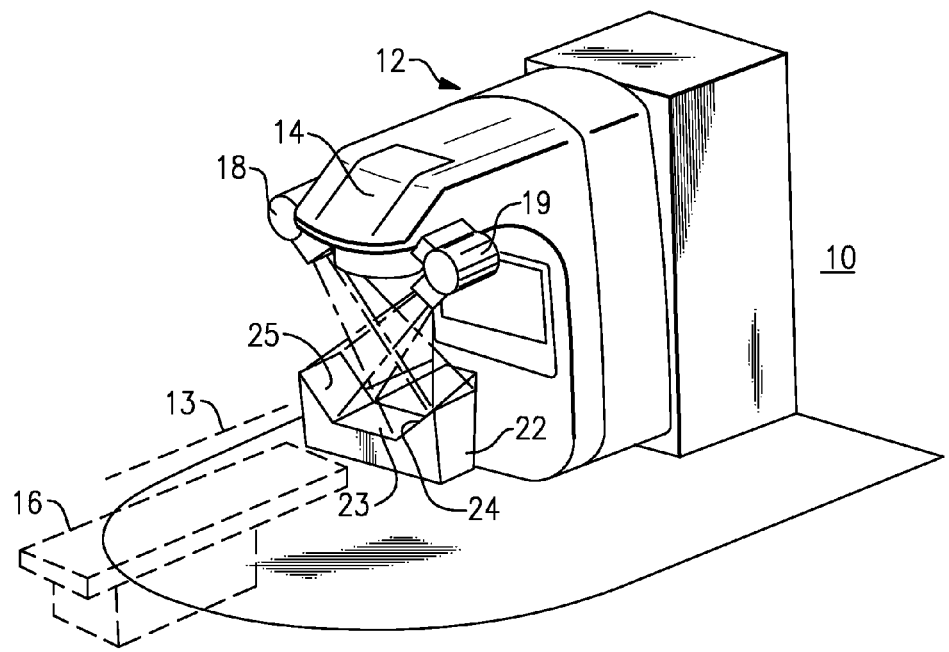
FIG.1
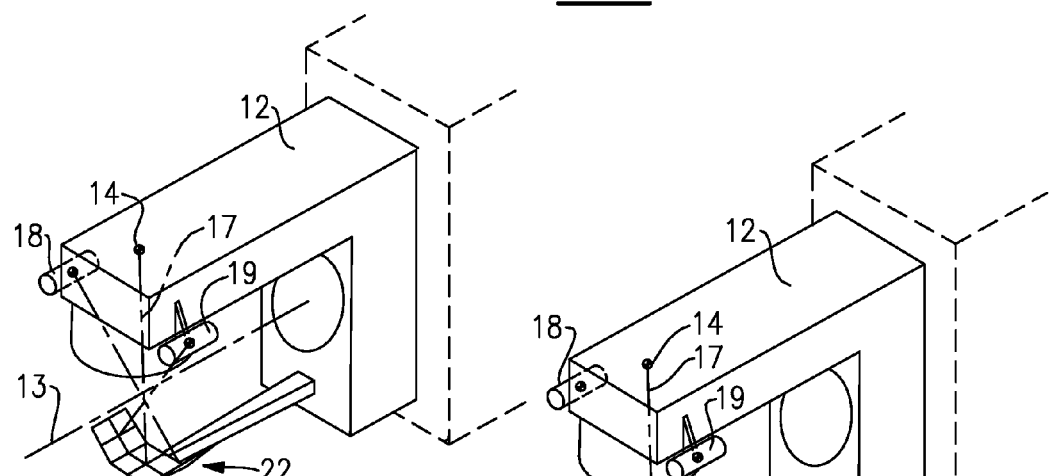
FIG.2
FIG.3

RADIATION THERAPY MACHINE WITH TRIPLE KV/MV IMAGING

BACKGROUND OF THE INVENTION

The present invention relates to radiology and radiotherapy, and is more particularly directed to imaging devices for aligning and monitoring a treatment radiation field relative to a planned treatment volume within a patient positioned on a treatment table or therapy couch. The invention is more specifically concerned with apparatus and technique for verifying patient position relative to the therapy beam treatment field, in real time or near real time, and to aid in effecting corrections of patient positioning for efficient and effective application of the therapy dose to the affected volume of the patient.

Radiation therapy involves application of one or more doses per treatment to a patient from high energy radiation from a therapy X-ray machine or from a linear accelerator, i.e., Clinac™. The strength of the radiation must be concentrated in a specific zone or volume, e.g., to shrink or eliminate a tumor, but the total radiation to which the patient is subjected must be kept as low as possible. In the current practice, prior to radiation therapy the patient can positioned on a simulator, that is, on a low-energy x-ray machine which is otherwise identical to the accelerator or treatment machine, and an x-ray image is taken, either on film or with a digital image sensor. The simulator image is used to identify the portion of the patient's body that is to receive the radiation treatment, as versus that which is to be spared or protected. The information obtained on the simulator can be used by the oncologist for prescribing the appropriate dosage, and he or she can outline how the treatment field is to be collimated. However, the collimation of the field is meant to be an exact measure, but because positioning a patient exactly the same on the therapy machine as on the simulator is inexact at best, it must be verified at the therapy machine prior to treatment. Moreover, with some patient treatment volumes there is always some movement of the patient's internal tissues (e.g., lungs and prostate) before and during treatment, due to the normal biological functions, i.e., respiration, blood circulation, gastro-intestinal movements, and the like. This can result in the prescribed dose being applied incorrectly to the treatment volume, which can subject the patient's surrounding tissues to unnecessary radiation.

Prior attempts to use the high energy radiation from the treatment machine to produce images have resulted in low resolution and poor contrast response. In many cases a flat panel imager has been employed for this purpose, but the imager produces only very faint images of the affected tissues, and the imager itself is eventually degraded or destroyed from bombardment with high energy radiation.

Because these images are of low quality and because of the time required to monitor the position of the applied dosage field, this approach has been regarded as unsatisfactory.

One useful approach to accurate patient positioning has been the portal imager, such as the radiation therapy imaging apparatus described in Chou et al. U.S. Pat. No. 4,995,068. This arrangement has helped to verify and to monitor position and alignment of the patient on a therapy machine. In this approach, a video camera is mounted on the counterweight side of the gantry, opposite the treatment head. An elongated light box is disposed over the camera to exclude ambient light from the camera. A fluoroscopic plate is positioned at the distal end of the light box, i.e., the end remote from the camera, and the plate is aligned with the treatment head, so it is on the vertical treatment axis, and diametrically opposite the therapy head. The plate produces a fluoroscopic image of the patient in response to radiation from the therapy beam that passes through the patient. A mirror in the light box is oriented to reflect the fluoroscopic image to the camera so that the treated volume of the patient and the shape of the therapy beam can be monitored on a viewing screen. The resulting image can be compared with a simulator image of the patient. The images can be enhanced for greater contrast, and can be stored for later reference. The electronic portal imaging device itself has reduced the amount of time required for the patient to be positioned and for the prescribed radiation dose to be applied at various angles to the affected area. This has resulted in sufficient time savings to accommodate an additional four patients per day per therapy machine. In addition, electronic portal imaging has made it possible to verify the beam shape and position relative to the patient position much more accurately than previously, thus avoiding radiating the healthy tissues that are nearby the affected volume.

There have also been proposals to mount low energy diagnostic radiation sources and imager sensors directly on the therapy machine to view the patient's treated volume while he or she is in position on the treatment table or couch, so that the patient's position can be verified. Some of these proposals have incorporated a pair of diagnostic radiation sources and a pair of sensor, so as to capture stereotactic information about the treated volume. Reiffel U.S. Pat. No. 6,118,848 shows a system for stabilizing target volume within a patient's body, where the target tissue, e.g., tumor, can change position due to normal body functions, such as respiration, blood flow, gastro-intestinal movement, etc. A pair of diagnostic x-ray sources are used, which are filtered to have different x-ray absorption edges. This is used to determine the location of image markers, such as gold seeds, balls or pins, from two different perspectives, to calculate the position of the treated volume in three-dimensional space. Rietzel Published Application US 2006/0067468 is directed to a radiotherapy system that includes a pair of low energy beam generators and a pair of image detectors, which are oriented on imaging axes that cross the isocentric axis, and these acquire data that can be used to locate the patient's treated volume in three dimensional space.

Neither of these employ an electronic portal imager device, and thus these designs cannot verify alignment of the patient's treated volume together with the footprint of the therapy beam.

Mansfield et al. U.S. Pat. No. 7,227,975 relates to a gantry-mounted stereoscopic imaging system in which there are first and second diagnostic radiation sources mounted on the sides of the therapy radiation source or head, first and second diagnostic imagers, and a therapeutic imager disposed diametrically opposite the therapy radiation source across the isocentric axis. Due to space limitations, the diagnostic imagers and the therapeutic imager cannot be used together. The therapy imager has to be moved out of the way for the diagnostic imagers to be placed into position for three-dimensional imaging of the patient's tumor. Then, the first and second diagnostic imagers, which are mounted on left and right retractable arms, have to be moved out of the way so that the therapy imager, i.e., portal imaging device, can be moved up into position. Some time is required for setting up these imaging devices, and in that time the patient can move, and normal body processes cause further displacement of the treated volume before the therapeutic dose can be administered.

OBJECTS AND SUMMARY OF THE INVENTION

Accordingly, it is an object of this invention to provide real time or near real time imaging for use in radiotherapy, with high-quality images that can be used for precise positioning of the patient.

It is another object to provide accurate verification of patient positioning before and during treatment, relative to the applied radiation dosage.

It is yet another object to provide visual alignment and shaping of the therapy radiation field, relative to the patient's treated volume.

It is a further object to provide real-time or near real-time therapy imaging with an imaging arrangement that is relatively compact and lightweight, and is of a straightforward, simple design.

It is still another object of this invention to acquire simultaneous information concerning the location of the patient's treated volume in three-dimensional space and concerning the shape and location of the therapy radiation field or beam.

It is a related object to provide a system that provides for correction of patient position, at the therapy console area, using this real-time acquired image information for accurate exposure of only the intended tissues to the therapeutic radiation.

In accordance with an aspect of the present invention, a triple-image radiation therapy imaging arrangement is associated with a radiation therapy apparatus, e.g., a linear accelerator, providing images of a patient prior to him or her being treated on the radiation therapy apparatus. This arrangement is effective for verification and monitoring of patient position and for verification of alignment and shaping of the radiation field. The radiation therapy apparatus rotates about an isocenter (which lies along an isocentric axis) on which a target volume of the patient is to be positioned for treatment. The radiation therapy apparatus has a gantry arrangement that permits the high-energy treatment head to be rotated around the isocenter. The treatment head applies the radiation dose to the patient positioned on a treatment table, radiating along the therapy beam central axis which passes through the isocenter. There are left and right diagnostic radiation sources mounted onto left and right sides of said treatment head. These diagnostic radiation sources each radiate along their respective diagnostic beam axes which pass through the mechanical isocenter. The triple-image radiation therapy imaging arrangement is mounted on the gantry arrangement generally opposite the therapy head, and includes a portal imager as well as left and right diagnostic image detectors. The portal imager has an image-forming plate, e.g., a scintillation plate or a fluoroscopic plate, positioned perpendicular to the therapy beam central axis, and is situated in a plane that is a given distance from the isocenter. The left and right diagnostic image detectors likewise each have an image-forming plate situated across the isocenter each corresponding to one of the two diagnostic radiation sources. The diagnostic image detector image forming plates are each situated in a plane that is the same given distance from the isocenter as the distance of the portal imaging plate.

Suitable video processing equipment, and suitable software are provided for capturing the images formed on the three image forming plates, and this equipment then outputs respective image signals. The image information is processed, and can produce video output signals that are conveyed to a viewing screen to display the positioning of the patient treatment field in respect to an irradiated volume of the patient. This equipment also includes an assistance module for assisting the linear accelerator therapist, at the treatment console position, in adjustment of the patient position via controlled movement of the treatment table, as a result of the information obtained from the captured images.

The left and right diagnostic imaging detectors are joined at one of their sides to left and right sides of the portal imaging detector, so the entire device is constructed as one unit.

The portal imaging detector image forming plate is favorably positioned substantially perpendicular to the central axis of the therapy beam, and likewise the left and right diagnostic imaging detector image forming plates are also positioned substantially perpendicular to the central axis of the respective diagnostic radiation sources.

In a preferred arrangement, the portal imaging detector image forming plate may incorporate a scintillation plate; and the portal imaging detector incorporates as well a camera that views along an optic axis, a mirror disposed on the optic axis to reflect an optical image formed on the scintillation plate, and a housing disposed over the scintillation plate, mirror and camera.

Favorably, each of the image forming plates of the left and right diagnostic imaging detectors may incorporate a fluoroscopic plate, and these detectors also may include a camera viewing along an optic axis, a mirror disposed along the optic axis to reflect an optical image formed on the fluoroscopic plate, and a housing disposed over the fluoroscopic plate, mirror and camera.

The above and many other objects, features, and advantages of this invention will become apparent to persons skilled in the art from the ensuing description of a preferred embodiment, which is to be read in conjunction with the accompanying Drawing.

BRIEF DESCRIPTION OF THE DRAWING

FIG. 1 is a perspective view of a radiation treatment machine on which is installed a triple image imaging apparatus according to one embodiment of this invention.

FIGS. 2 and 3 are basic perspective views for explaining operation of this embodiment.

DETAILED DESCRIPTION OF THE PREFERRED EMBODIMENTS

Figure 4:
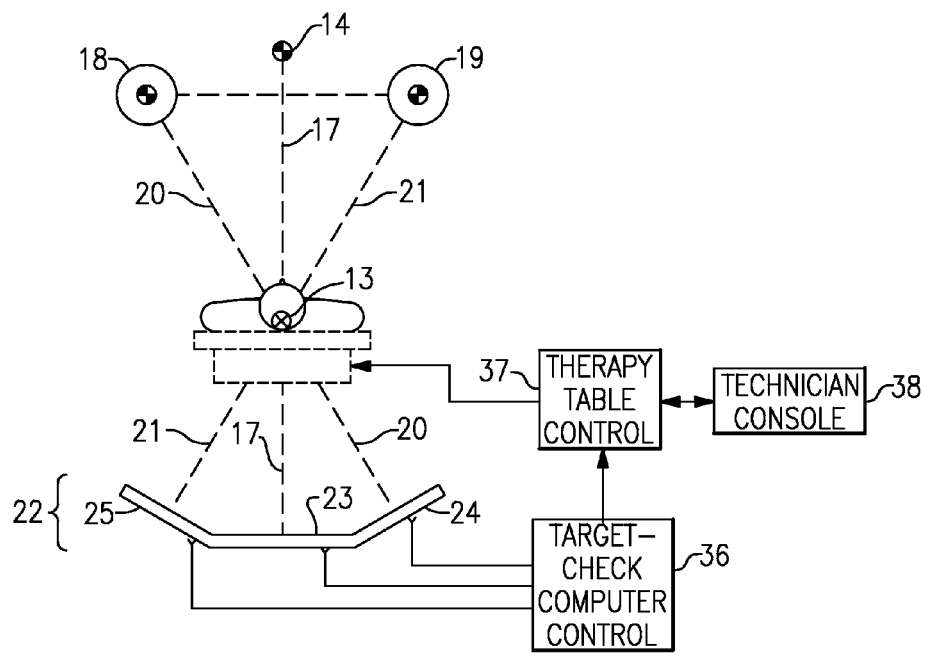
FIG. 4 is a schematic view of this embodiment.

With reference to the Drawing, and initially to FIG. 1, a radiology treatment or therapy machine 10 is shown to have a gantry 12 which rotates about an axis 13 of the mechanical isocenter. A high energy radiotherapy treatment head 14, e.g., with an energy of up to 25 Mev, is mounted on the gantry 12 and positioned to emit the radiotherapy beam radially across the axis 13 of the isocenter. A treatment table or couch 16 is provided to place the patient in a proper position for administration of the dose to the patient's affected tissues, so that the table presents the patient relative to the radiotherapy isocenter. The megavolt (Mev) radiotherapy head 14 emits its energy along a beam axis 17 that passes through the patient on the table 16.

A pair of lower energy kilovolt (kV) radiation sources 18 and 19, that is, diagnostic x-ray sources, are mounted on left and right sides of the radiotherapy head 14, and each of these directs its radiation vertically along its respective diagnostic central through the patient. These sources 18, 19 produce radiation in the kilovolt range, of the level typically used for diagnostic imaging of bony structures. As is the usual practice, the diagnostic sources are provided with shielding and collimation to confine the radiation fields. The radiation from the sources have respective beam axes 20, 21 that intersect the therapy machine isocenter at the same location as the beam axis 17 of the head 14. By design, each of the radiation sources 18 and 19 is at the same distance from the isocenter as is the radiotherapy head 14.

A triple-imager radiotherapy detector assembly 22 is mounted onto a counterweight side of the gantry 12 diametrically opposite the radiotherapy head 14. In this assembly 22, there are three image detectors associated respectively with (A) the two diagnostic radiation sources 18, 19 and with (B) the radiotherapy head 14, and positioned perpendicular to the respective beam axes 20, 21, and 17. The assembly 22 is a fully integrated kV/Mev triple imager detector system that acquires stereographic images of the patient for instantaneous comparison with a synchronously acquired Mev portal image for patient position verification and adjustment prior to treatment. That is, the triple image detector assembly 22 is made up of three detectors: two for acquiring the 3-dimensional image formed from the diagnostic x-ray beams and one for acquiring the portal image from the therapy beam.

The radiation therapy machine 10 is illustrated schematically in FIGS. 2 and 3, and the three imager detector assembly 22 is shown in a simplified form, with the three image-forming plates 23, 24, 25 supported from the counterweight portion of the gantry 12 at a position beneath the couch 16.

Figure 5:
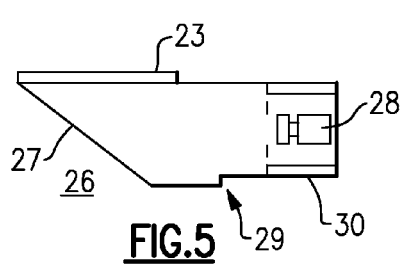
FIG. 5 is a schematic elevational view of a portal imager device used in this embodiment.
Figure 6:
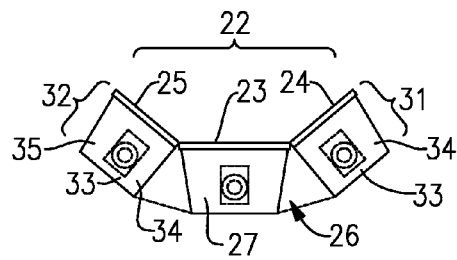
FIG. 6 is a schematic end view of the triple imager device of this embodiment.

A practical embodiment of the assembly 22 is illustrated in FIGS. 5 and 6. At the center is a portal imaging assembly 26, which can be constructed as generally shown in U.S. Pat. No. 4,995,068. The scintillation plate 23 is disposed at the distal end and oriented substantially perpendicular to the therapy beam central axis, and a mirror 27 is disposed beneath the plate 23 to reflect the light from the plate to follow the generally horizontal optical axis of a camera 28 that is mounted at the proximal end of the assembly 26, i.e, adjacent the therapy gantry counterweight. The camera may be provided with liquid cooling. A light-tight shroud or casing 29 covers the camera 28 and mirror 27, to eliminate ambient light, and a radiation shield 30 is provided at the proximal end of the shroud, to shield the camera from radiation.

Immediately adjacent the portal imager assembly 26, at its left and right sides, are first and second diagnostic imaging assemblies 31 and 32. Each of these assemblies comprises the respective fluoroscopic plate 24, 25, as well as an associated camera 33, mirror 34 and light-tight shroud 35. A radiation shield may also be provided at the camera end of each of the diagnostic imaging assemblies. In each case, the mirror reflects the image formed on the fluoroscopic plate along the optical axis of the associated camera, which is horizontally oriented at the gantry end of the diagnostic imaging assembly.

The diagnostic imaging plates or fluoroscopic plates 24, 25 are situated with their side edges abutting a respective side edge of the portal imager scintillation plate 23. The fluoroscopic plates and the scintillation plate are each positioned at the same distance from the kV imaging sources, and each of them is positioned substantially perpendicular to the respective source, i.e., diagnostic sources 17 and 18, and therapy source 14, that is, each of the plates is square to the respective radiation beam central axis. Each of the images produced from the triple detector assembly 22 is thus the same size and orientation, but from a different perspective.

Another type of imaging plate could be used in place of the scintillation plate or fluoroscopic plates discussed just above, for example, a solid-state flat panel imager may be employed, at least for the diagnostic imagers, i.e., image producing plates 24 and 25.

As shown generally in FIG. 4, the image information from the triple image detector assembly 22 may be provided, as three separate image signals, to a TargetCheck™ control computer 36, which may be located in an adjacent room. The arrangement may be as generally shown in U.S. Pat. No. 4,995,068. The three images obtained provide stereotactic information concerning the position of the target volume within the patient relative to the therapy machine mechanical isocenter, and also provide the location and shape of the therapy beam relative to the target volume to be treated. The acquired data are provided to a therapy table control 37 that is coupled to a therapy operator console 38, located outside the patient treatment room. The computer 36 includes a couch setup assistant software module, that compares position of the patient's treated volume with the position and shape of the therapy beam, and can indicate adjustments for the therapist to make in the table position to align the patient target volume with the therapy beam. This may involve moving the table up or down, right or left, or forward or reverse, and may effect corrections as small as a millimeter.

The radiotherapy arrangement 10 of this invention with the triple imager assembly 22, providing a therapy portal image and associated diagnostic images, allowing for patient positioning adjustment outside the treatment room on the therapy console at the console area, achieves a total integrated functionality. This arrangement both records and monitors patient position and treatment beam shape. This arrangement also permits the radiotherapy machine to take full advantage of powerful software tools, including the couch setup assistant, dosimetry modules, pre-treatment verification modules, automated seed/marker recognition, and a real-time physician approval module. No other radiotherapy arrangement employs a triple-imager to provide instantaneous, real-time capture of patient positioning and therapy beam shape.

With the triple-imager detector arrangement of this invention, the dual diagnostic (kV) imagers verify the patient position, and the portal (Mev) imager verifies field shape, serves as pre-treatment verification of field position relative to patient's treatment volume, and provides fluence mapping of the treatment dose.

The triple-imager detector assembly 22 can be employed with any radiotherapy machine or linear accelerator. While the radiotherapy machine illustrated here has an L-shaped gantry 12, other linear accelerators may have other structure that serves the purpose of the gantry. For example, the radiotherapy machine may employ a ring gantry or another shape. The type of gantry would not affect the principles or operation of this invention.

While the invention has been described in detail with respect to one preferred embodiment, it should be recognized that there are many alternative embodiments that would become apparent to persons of skill in the art. Many modifications and variations are possible which would not depart from the scope and spirit of this invention, as defined in the appended claims.

We claim:

1. Unitary triple imager radiation therapy imaging arrangement for providing images of a patient being treated on a radiation therapy apparatus for verification and monitoring of patient positioning and verification of alignment and shaping of the radiation field of the radiation therapy apparatus, wherein said radiation therapy apparatus has a mechanical isocenter onto which a treatment volume of the patient is to be positioned for treatment, and which includes a high-energy treatment head for applying a radiation dose to a patient positioned on a treatment table, and radiating from a therapy beam radiation source in said head along a therapy beam axis that passes through said mechanical isocenter;

left and right diagnostic radiation sources mounted onto left and right sides of said treatment head, each radiating along a respective diagnostic beam axis that passes through said isocenter; and a gantry rotatable about said isocenter and carrying said treatment head for permitting said radiation dose to be applied to the patient from any of a range of angles about said isocenter;

the triple imager radiation therapy imaging arrangement being mounted on said gantry apparatus and including a portal imaging detector having an image-forming plate situated substantially perpendicular to the therapy beam axis, and being situated in a plane that is a given distance from the therapy beam source in said therapy head;

left and right diagnostic image detectors each having an image forming plate situated substantially perpendicular to a respective one of said diagnostic beam axes, each of said diagnostic image detectors being situated in a plane that is at said given distance from the respective diagnostic source;

means for capturing the images formed on said image forming plates and outputting respective image signals; and means conveying the output image signals to a viewing screen to display the positioning of the radiation field in respect to a treatment volume of the patient; and means for permitting pretreatment adjustment of the position of said patient on said treatment table in response to said captured images.

2. Triple imager radiation therapy imaging arrangement according to claim 1, wherein said portal imaging detector image forming plate is oriented substantially perpendicular to the beam central axis of said therapy beam, and said left and right diagnostic imaging detector image forming plates are oriented substantially perpendicular to the beam central axes of the respective diagnostic radiation sources.

3. Triple imager radiation therapy imaging arrangement according to claim 1, wherein said portal imaging detector image forming plate includes a scintillation plate; and said portal imaging detector also includes a camera viewing along an optic axis, a mirror disposed along said optic axis reflecting an optical image formed on said scintillation plate, and a housing disposed over said scintillation plate, said mirror and said camera.

4. Triple imager radiation therapy imaging arrangement according to claim 1, wherein each of said image forming plates includes a fluoroscopic plate, and each said diagnostic imaging detector includes a camera viewing along an optic axis, a mirror disposed along said optic axis reflecting an optical image formed on said fluoroscopic plate, and a housing disposed over said fluoroscopic plate, said mirror and said camera.

5. Unitary triple imager radiation therapy imaging arrangement for providing images of a patient being treated on a radiation therapy apparatus for verification and monitoring of patient positioning and verification of alignment and shaping of the radiation field of the radiation therapy apparatus, wherein said radiation therapy apparatus has a mechanical isocenter onto which a treatment volume of the patient is to be positioned for treatment, and which includes a high-energy treatment head for applying a radiation dose to a patient positioned on a treatment table, and radiating along a therapy beam axis that passes through said mechanical isocenter;

left and right diagnostic radiation sources mounted onto left and right sides of said treatment head, each radiating along a respective diagnostic beam axis that passes through said isocenter; and a gantry rotatable about said isocenter and carrying said treatment head for permitting said radiation dose to be applied to the patient from any of a range of angles about said isocenter; the triple imager radiation therapy imaging arrangement being mounted on said gantry apparatus and including a portal imaging detector having an image-forming plate situated substantially perpendicular to the therapy beam axis, and being situated in a plane that is a given distance from the therapy head;

left and right diagnostic image detectors each having an image forming plate situated substantially perpendicular to a respective one of said diagnostic 24 beam axes, each of said diagnostic image detectors being situated in a plane that is at said given distance from the respective diagnostic source;

means for capturing the images formed on said image forming plates and outputting respective image signals; and means conveying the output image signals to a viewing screen to display the positioning of the radiation field in respect to a treatment volume of the patient; and means for permitting pre-treatment adjustment of the position of said patient on said treatment table in response to said captured images, wherein said left and right diagnostic imaging detectors are joined at sides thereof to left and right sides of said portal imaging detector.

6. Unitary triple imager radiation therapy imaging arrangement for providing images of a patient being treated on a radiation therapy apparatus for verification and monitoring of patient positioning and verification of alignment and shaping of the radiation field of the radiation therapy apparatus, wherein said radiation therapy apparatus has a mechanical isocenter onto which a treatment volume of the patient is to be positioned for treatment, and which includes a high-energy treatment head for applying a radiation dose to a patient positioned on a treatment table, and radiating along a therapy beam axis that passes through said mechanical isocenter, left and right diagnostic radiation sources mounted onto left and right sides of said treatment head, each radiating along a respective diagnostic beam axis that passes through said isocenter, and a gantry rotatable about said isocenter and carrying said treatment head for permitting said radiation dose to be applied to the patient from any of a range of angles about said isocenter;

the triple imager radiation therapy imaging arrangement being mounted on said gantry apparatus and including a portal imaging detector having an image-forming plate situated substantially perpendicular to the therapy beam axis, and being situated in a plane that is a given distance from said mechanical isocenter;

left and right diagnostic image detectors each having an image forming plate situated substantially perpendicular to a respective one of said diagnostic beam axes, each of said diagnostic image detectors being situated in a plane that is at said given distance from said mechanical isocenter;

means for capturing the images formed on said image forming plates and outputting respective image signals; and means conveying the output image signals to a viewing screen to display the positioning of the radiation field in respect to a treatment volume of the patient; and means for permitting pre-treatment adjustment of the position of said patient on said treatment table in response to said captured images.

* * * * *